US010758275B2

(12) United States Patent
Krüger

(10) Patent No.: US 10,758,275 B2
(45) Date of Patent: Sep. 1, 2020

(54) PEDICLE SCREW WITH SCREW-IN AID

(71) Applicant: Aesculap AG, Tuttlingen (DE)

(72) Inventor: Sven Krüger, Trossingen (DE)

(73) Assignee: AESCULAP AG, Tuttlingen (DE)

( * ) Notice: Subject to any disclaimer, the term of this patent is extended or adjusted under 35 U.S.C. 154(b) by 38 days.

(21) Appl. No.: 15/318,549

(22) PCT Filed: Jun. 12, 2015

(86) PCT No.: PCT/EP2015/063140
§ 371 (c)(1),
(2) Date: Dec. 13, 2016

(87) PCT Pub. No.: WO2015/193178
PCT Pub. Date: Dec. 23, 2015

(65) Prior Publication Data
US 2017/0128103 A1    May 11, 2017

(30) Foreign Application Priority Data

Jun. 20, 2014 (DE) .................. 10 2014 108 705

(51) Int. Cl.
*A61B 17/70* (2006.01)
*A61B 17/86* (2006.01)
*F16B 35/04* (2006.01)

(52) U.S. Cl.
CPC ........ *A61B 17/7032* (2013.01); *A61B 17/866* (2013.01); *A61B 17/8665* (2013.01); *F16B 35/047* (2013.01)

(58) Field of Classification Search
CPC ...... A61B 17/7032–704; A61B 17/866; A61B 17/8665; F16B 35/047

USPC .......... 606/300–321, 246–279; 411/307, 437
See application file for complete search history.

(56) References Cited

U.S. PATENT DOCUMENTS

| | | | |
|---|---|---|---|
| 6,817,816 B2* | 11/2004 | Hill | F16B 37/005 411/309 |
| 2002/0128657 A1 | 9/2002 | Hansson | |
| 2003/0171755 A1* | 9/2003 | Moseley | A61B 17/7032 606/270 |
| 2005/0182410 A1* | 8/2005 | Jackson | A61B 17/7032 606/278 |
| 2005/0216000 A1 | 9/2005 | Colleran | |
| 2006/0083603 A1 | 4/2006 | Jackson | |

(Continued)

FOREIGN PATENT DOCUMENTS

| | | |
|---|---|---|
| DE | 19912364 | 10/2000 |
| DE | 202005007495 | 8/2005 |

(Continued)

OTHER PUBLICATIONS

International Search Report and Written Opinion for International Application PCT/EP2015/063140, dated Sep. 16, 2015, 9 pages.

(Continued)

*Primary Examiner* — Jessica Weiss

(57) ABSTRACT

A bone screw includes a receiving sleeve having a sleeve wall which forms a seat for a longitudinal support for the surgical connection of adjacent bone screws. The bone screw includes an internal thread. A thread turn of the internal thread has a widened lead-in region on the thread lead-in side.

18 Claims, 3 Drawing Sheets

(56) References Cited

U.S. PATENT DOCUMENTS

| | | | | |
|---|---|---|---|---|
| 2009/0318970 | A1* | 12/2009 | Butler | A61B 17/7032 606/264 |
| 2011/0152947 | A1* | 6/2011 | Kirschman | A61B 17/7032 606/302 |
| 2011/0318136 | A1* | 12/2011 | Toyonaga | F16B 35/047 411/366.1 |
| 2013/0079830 | A1* | 3/2013 | Garamszegi | A61B 17/7011 606/305 |
| 2013/0274815 | A9* | 10/2013 | Jackson | A61B 17/7035 606/304 |
| 2014/0018867 | A1 | 1/2014 | Freudiger | |
| 2014/0214097 | A1* | 7/2014 | Jackson | A61B 17/7037 606/305 |

FOREIGN PATENT DOCUMENTS

| | | |
|---|---|---|
| EP | 2258289 | 12/2010 |
| WO | 2012103660 | 8/2012 |

OTHER PUBLICATIONS

German Search Report for German Application No. 10 2014 108 705.4, dated Dec. 22, 2014 with translation, 13 pages.

\* cited by examiner

PEDICLE SCREW WITH SCREW-IN AID

RELATED APPLICATION(S)

This application is the United States national phase entry under 35 U.S.C. § 371 of International Patent Application No. PCT/EP2015/063140, filed Jun. 12, 2015, which is related to and claims the benefit of priority of German Patent Application No. DE 10 2014 108 705.4, filed Jun. 20, 2014. The contents of International Patent Application No. PCT/EP2015/063140 and German Patent Application No. DE 10 2014 108 705.4 are incorporated by reference herein in their entireties.

FIELD

The present invention relates to a bone screw system, especially a pedicle screw system, comprising a bone screw or a pedicle screw, resp., a receiving sleeve and a clamp screw adapted to be screwed into the latter, wherein the receiving sleeve includes a sleeve wall which forms a seat for a longitudinal support for the surgical connection of adjacent bone screws or, resp., pedicle screws and is provided with an internal thread, wherein the clamp screw is provided with an external thread and is adapted to be screwed into the internal thread of the receiving sleeve.

BACKGROUND

Bone screws and pedicle screws are known from the state of the art. They serve, for example, for the dorsal stabilization of the spinal column by means of transpedicular screwing. Pedicles screws are placed in the pedicles of adjacent vertebrae, whereupon an angularly stable connection is made between the pedicle screws which are axially superimposed and an axially extending longitudinal support or land. The pedicle screws and the longitudinal supports form a vertebral stabilizing system.

Usually a pedicle screw includes a screw shank extending in the axial direction and including an external thread to which a receiving sleeve, the so called tulip, is connected on the side of the screw head. Said tulip is substantially U-shaped having opposed wall portions and a gap formed therebetween and extending in the radial direction for the longitudinal support or land. An internal thread extending in the axial direction is introduced into the tulip. The longitudinal support is inserted in the gap of the tulip in the radial direction and is fixed by means of a locking element or a clamp screw, typically in the form of a stud screw or threaded nut, which is also referred to as set screw and is screwed into the internal thread.

When a set screw is attached to a pedicle screw, especially in the case of an open operation there is a risk of jamming due to tilted attachment of the set screw. This situation occurs in particular when the thread of the set screw and the internal thread of the tulip are twisted about approx. 180° when the set screw is attached, i.e. a threaded flank abuts a threaded flank, as illustrated in the enclosed FIG. 1.

In the case of known pedicle screws, even when the set screw is correctly attached, slight tilting or jamming of the set screw relative to the axis of the pedicle screw and, resp., the tulip thereof may entail a "rough" attachment, which increases the risk of jamming. To make matters worse, in practical use the set screw is usually pressed onto the tulip with a certain force. Said axial pre-force may detrimentally result already in the set screw getting jammed with respect to the tulip, as the planar upper side of the tulip usually does not correspond to the thread geometry of the set screw.

Jamming may lead to the thread chamfer, especially the one of the set screw, being damaged. In the worst case, a so called "cross-threading" may occur, meaning that the set screw is tilted with respect to the longitudinal axis of the screw shank and the external thread thereof so far that the thread start of the set screw, viz. the lead-in thread turn or turns, engage(s) in the wrong thread turn of the internal thread of the tulip, which may lead to damage of the thread up to uselessness of the set screw and/or of the pedicle screw. A clicking when attaching the set screw which is caused by jamming will unsettle the user. The latter is not sure whether the thread has been damaged.

In order to reduce the afore-described problems, particular thread designs such as e.g. rectangular threads or undercut threads are known and are described to "reduce cross-threading". However, correct attachment of the set screw appears to be the crucial action for avoiding damage of threads. For this purpose, pedicle screw systems are known in which a rotatable guide cap is mounted on the set screw and enables the set screw to be additionally guided in the tulip head thread. It is moreover known to chamfer the thread lead-in of the set screw, in other words to reduce the thickness thereof. In this way, engagement of the thread lead-in of the set screw into the thread lead-in of the tulip head is facilitated. Apart from that, there are systems offering a guide for the set screw so as to prevent the same from tilting with respect to the screw axis. This guide subsequently will be broken away. During percutaneous operation the coupled sleeve may prevent the set screw from tilting in numerous cases. During open operation a set screw starter instrument including a guiding sleeve aligning relative to the body may limit such problematic tilting.

The afore-described pedicle screw systems known from the state of the art are disadvantageously cost-intensive and complex. As a rule, they are not adapted to facilitate and reliably ensure correct attachment of a set screw to a pedicle screw. A screw driver including a guiding sleeve may prevent tilting to a restricted extent only, as said guiding sleeve requires a certain play for coupling. In addition, said sleeve restricts the surgeon's vision onto the bone or pedicle screw. An optimization of the chamfer improves finding the thread, but jamming may occur despite this measure. Jamming of a "chamfered" set screw is critical, as the latter may be damaged very easily due to the smaller wall thickness.

SUMMARY

Based on the afore-described state of the art, the object underlying the invention is to provide a bone screw system, especially a pedicle screw system, which facilitates and renders the correct attachment of a set screw to a bone or pedicle screw safer without any additional elements such as guiding sleeves etc. being required or the vision of the operating surgeon being reduced.

According to the present invention, this object is achieved by a bone screw system or, resp., pedicle screw system, wherein a thread turn of the internal thread on the lead-in side includes a widened lead-in region.

The present description is made with reference to a bone screw system and a bone screw, respectively. However, the invention relates especially to a pedicle screw system and a pedicle screw, respectively. The term bone screw is therefore meant to designate a pedicle screw and vice versa.

In accordance with the invention, the lead-in region is widened as compared to the residual and usual run of the thread turn. The internal thread of the receiving sleeve as well as the external thread of the clamp screw may be single-start or multi-start threads. In the case of multi-start threads it is of particular advantage when each thread turn includes a widened lead-in region and is widened on the lead-in side.

It is advantageously achieved by the widened lead-in region that the cross-sectional window available for engagement in a lead-in thread land of the clamp screw is increased vis-à-vis screw systems known from the state of the art. Even if the clamp screw is attached to the receiving sleeve in a tilted manner, i.e. in the case of attachment with non-aligned axes, there will be no "seizing" of the external thread and the internal thread. Rather, the external thread of the clamp screw may enter into the internal thread without any damaging contact with a threaded flank of the latter. Depending on the size of widening, the clamp screw may tilt without damage vis-à-vis the receiving sleeve with the alignment of the axes of the clamping screw and the receiving sleeve deviating more or less strongly. It is a particular advantage of the invention that with an increasing screwing depth into the internal thread the clamp screw gets aligned relative to the receiving sleeve. Such alignment is advantageously carried out automatically until the axes of the clamp screw and the receiving sleeve are aligned and the clamp screw is located straightly and correctly within the internal thread. Therefore it is no longer required for an operating surgeon to turn special attention to non-tilted attachment of the set screw, which considerably alleviates work and entails benefits in terms of time-saving.

The widened thread entry or thread turn start so-to-speak forms sort of a ramp in order to guide or lift a clamp screw or set screw initially obliquely attached or tilted during attachment, when it is further screwed into the actual thread turn, and to align the clamp screw or set screw again coaxially with respect to the internal thread of the receiving sleeve.

Preferably, the lead-in region is widened in the axial direction. Such widening especially efficiently prevents jamming or tilting of the clamp screw with respect to the axis of the receiving sleeve. Alternatively or additionally, the widening of the lead-in region may be formed in the radial direction, which brings about an especially simple positioning of the clamp screw in the radial direction relative to the receiving sleeve. This is of advantage especially for operations offering a strongly reduced vision.

In an embodiment the lead-in region includes a flank. Said flank may be inclined in the peripheral direction vis-à-vis the flank in the further run of the residual thread turn, i.e. outside the lead-in region. It may have a smaller inclination than the residual thread turn, but it may also rise especially into the internal thread. Preferably it is the flank of the lead-in region facing the threaded base. The inclination of the flank in the case of the flank facing the threaded base is preferably flatter and in the case of the flank facing the thread entry is preferably steeper than the inclination of the flank in the further run of the residual thread turn. It may correspond especially to 0.5 to 0.9 times, more preferably to 0.6 to 0.8 times and especially preferred to 0.7 times the inclination of the flank in the residual run of the thread turn. In the case of the flank facing the thread entry the respective inverse values are applicable. These inclinations enable the clamp screw to be easily aligned during screwing into the internal thread and at the same time prevent the threaded flanks from being excessively weakened and the internal and external threads from being seized. It is within the scope of the invention when both flanks of the lead-in region, i.e. the flank facing the threaded base and the flank facing the threaded lead-in, are configured in the aforementioned shape with deviating inclination. In this way, the lead-in window may be very large.

In particular, the cross-section of the thread turn, especially the cross-section in the radial direction, may correspond at the thread lead-in to 1.7 to 1.2 times, preferably to 1.6 to 1.3 times and especially preferred to 1.5 to 1.4 times the cross-section of the thread turn outside the lead-in region. Furthermore, the thickness in the axial direction of a threaded land provided between the lead-in region and an adjacent thread turn may be reduced as compared to the thickness of a threaded land between adjacent thread turns by less than 50%, preferably by less than 35% and especially preferred by less than 20%.

According to the invention, the lead-in region may extend into the internal thread differently far in the circumferential direction. It is preferred when the lead-in region extends in the circumferential direction over a radial portion between approx. 20° and approx. 135°, preferably between approx. 40° and approx. 115°, more preferred between approx. 60° and approx. 90°. In this way, the clamp screw finally is not aligned before it is screwed sufficiently far into the internal thread for required support inside the same so that repeated jamming or release of the clamp screw can be safely prevented. Moreover, the load capacity of the thread is weakened, as is inevitable by forming the lead-in region, only over a small part of the thread so that with particular advantage the load capacity of the thread remains almost unchanged.

In an embodiment of the invention the internal thread of the receiving sleeve and/or the external thread of the clamp screw is/are an undercut thread, especially an undercut buttress thread. The thread turn may as well have a T-shaped or L-shaped cross-section. This may especially cause the clamp screw to be clamped or secured inside the internal thread.

The screw system according to the invention may be a mono-axial or poly-axial system. This is to say that the receiving sleeve may be formed integrally with the bone screw or that the receiving sleeve may be adapted to be positioned as a separate element, especially arranged at an angular position relative to the bone screw on the latter. In the case of a mono-axial bone screw, the receiving sleeve is tightly connected to the shank thereof, for example manufactured in one piece, welded or soldered. In the case of a poly-axial bone screw, said screw may have an external thread portion manufactured as a separate shank component and having a spherical or (semi)-spherical screw head. The receiving sleeve may be arranged on the same to be adapted to be angularly positioned. The receiving sleeve may engage behind the screw head in the transitional area to the bone screw shank. In this way the receiving sleeve may be pivoted and/or rotated relative to the shank after screwing the bone screw into a bone so as to obtain a desired position and alignment substantially independently of the alignment of the shank. The undercut prevents the receiving sleeve from being removed from the shank head. Subsequently, the receiving sleeve can be fixed in position on the screw head of the bone screw by means of the clamp screw with the longitudinal support/land being interposed or by means of an additional screw element.

The object stated in the beginning is moreover achieved by a method of manufacturing a bone screw system according to the invention, especially a bone screw system according to any one of the enclosed claims, wherein the widening in the lead-in region is formed by milling, especially by milling the widening into the already formed thread turn, preferably by means of a T-groove cutter.

BRIEF DESCRIPTION OF THE DRAWING FIGURES

Further features and advantages of the present invention will be evident from the following exemplary and non-limiting description of the invention by way of a pedicle screw system as an example of a bone screw system by way of Figures. These Figures are merely schematic and merely serve for the comprehension of the invention, wherein.

DETAILED DESCRIPTION

Figure 1:
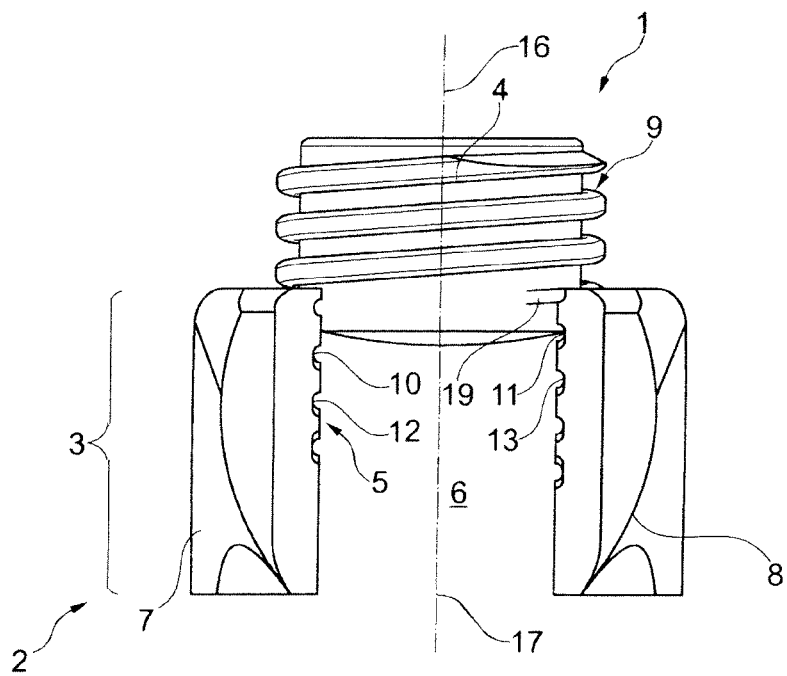
FIG. 1 shows a cutout of a pedicle screw system showing the head area as an example of a bone screw system in a lateral view.

FIG. 1 illustrates the head area of a pedicle screw system 1 in a lateral view. The pedicle screw system 1 includes a pedicle screw 2, a receiving sleeve 3 and a clamp screw 4. The receiving sleeve 3 basically may be formed integrally with the pedicle screw 2 as a so called tulip or as a separate component. The latter may be arranged to be movable on the pedicle screw 2 so that a poly-axial pedicle screw system is formed in which the receiving sleeve 3 is adapted to be angularly positioned relative to the pedicle screw 2. The following description will be given with reference to a receiving sleeve 3 formed integrally with the pedicle screw 2; it is also applicable to a poly-axial pedicle screw system, however.

The pedicle screw 2 is provided on the side opposed to the receiving sleeve 3 with an external thread not shown in the Figures by which it is adapted to be screwed into a pedicle canal of a vertebra (as an example of a bone). For this purpose, on the side of the receiving sleeve 3 the pedicle screw 2 is provided with a screwdriver engagement not shown in the Figures. The receiving sleeve 3 is substantially U-shaped including a hole 6 introduced in the same in the axial direction and including an internal thread 5. In other words, the receiving sleeve 3 may be formed by removing material from a hollow cylinder on radially opposed sides in the axial direction and providing the hole of the hollow cylinder with the internal thread 5. Two radially opposed sleeve wall portions 7, 8 whose inner surfaces facing each other delimit the hole 6 and are provided with the internal thread 5 are retained from the hollow cylinder.

The clamp screw 4 in the form of a stud screw common for this purpose is provided with an external thread 9 and a front-face tool holder, for example a hexagonal recess, which is not shown in the Figures.

Figure 2:
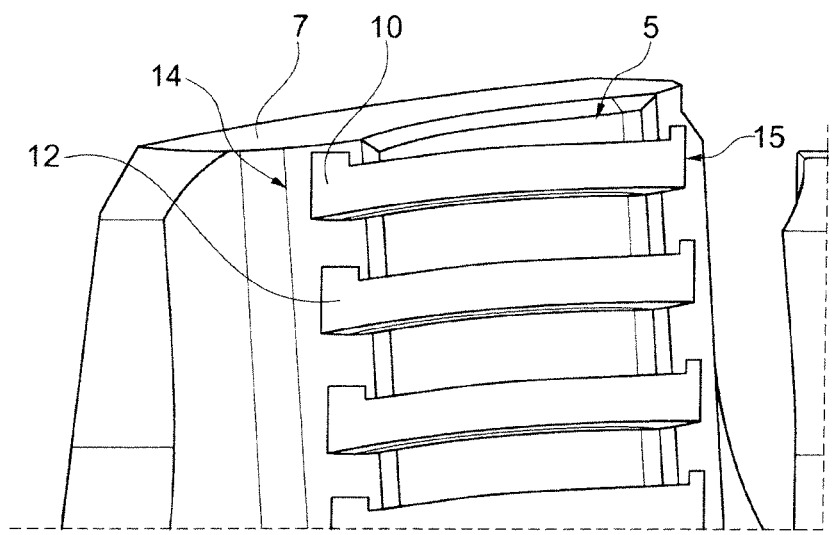
FIG. 2 shows a perspective representation of an internal thread of a pedicle screw head known from the state of the art.

FIG. 2 shows the internal thread 5 of a pedicle screw system 1 as known from the state of the art. The internal thread 5 is configured to be a single-start thread. It has one single thread turn including a first thread portion 10 in the first sleeve wall portion 7, a second thread turn portion 11 in the opposite sleeve wall portion 8, a third thread turn portion 12 in the first sleeve wall portion 7, a fourth thread turn portion 13 again provided in the opposite sleeve wall portion 8 etc. The thread turn portions 10, 12 in the first sleeve wall portion 7 comprise a lead-in side 14 and a lead-out side 15. The thread turn portions 11, 13 in the second sleeve wall portion 8 equally comprise a lead-in side and a lead-out side.

FIG. 1 illustrates the clamp screw 4 at the beginning of screwing into the receiving sleeve 3. It is clearly visible that for correctly screwing its external thread 9 into the internal thread 5 the clamp screw 4 has to be aligned relative to the receiving sleeve 3 such that the axis 16 of the clamp screw 4 is congruent with the axis 17 of the internal thread 5. FIG. 1 shows such positioning. It is obvious that especially in the case of polygonal pedicle screws and/or with a reduced vision and/or with poor accessibility such positioning may be very problematic.

Figure 3:
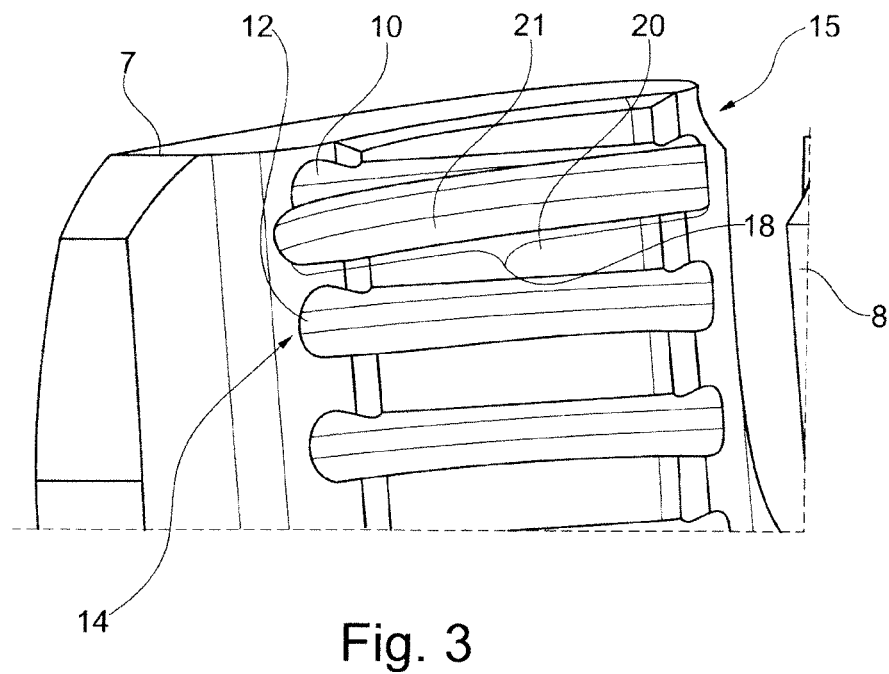
FIG. 3 shows a perspective view of an internal thread of a pedicle screw head according to the invention.
Figure 4:
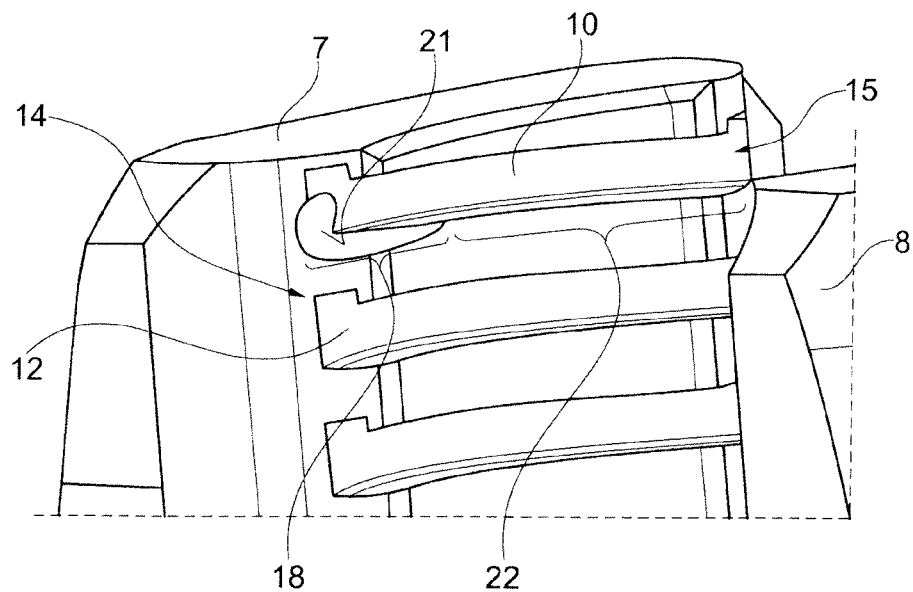
FIG. 4 shows a further embodiment of the internal thread according to the invention in a perspective view.
Figure 5:
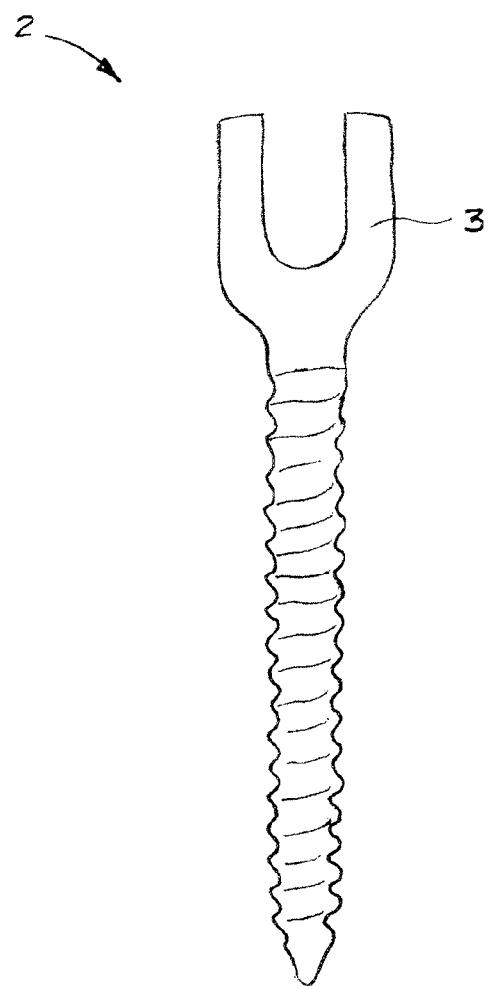
FIG. 5 shows a perspective view of a receiving sleeve formed integrally with a bone screw head.

FIGS. 3 and 4 illustrate a lead-in region 18 of the internal thread 5 of the receiving sleeve 3 configured according to the invention in two different embodiments. In the embodiment of FIG. 3 the lead-in region 18 extends over the entire peripheral length of the first thread turn portion 10. When comparing the first thread turn portion 10 to the third thread turn portion 12 configured in a conventional way, it becomes obvious that the cross-section of the thread turn portion 10 is widened in the axial direction as compared to a first thread turn portion 10 configured in a conventional manner (cf. e.g. FIG. 1). In the shown embodiment only the first thread turn portion 10 is widened in this way, while the other thread turn portions 11, 12, 13 etc. conventionally have a constant cross-section. It is achieved in an advantageous manner by the widened lead-in region 18 that the cross-sectional window available for engagement with the lead-in thread land 19 of the clamp screw 4 is enlarged as compared to the state of the art. Even in the case of a tilted attachment of the clamp screw 4 to the receiving sleeve 3, i.e. in the case of attachment with non-aligned axes 16, 17, no "seizing" of the external thread 9 and the internal thread 5, and especially of the lead-in thread land 19 and the flank 21 of the first thread turn portion 10 can occur. Rather, the lead-in thread land 19 may enter without any damaging contact with the thread flank of the first thread turn portion 10 into the latter from the lead-in side 14, namely depending on the size of the widening with more or less strongly deviating alignment of the axes 16, 17. With an increasing screwing depth into the internal thread 5, the clamp screw 4 is aligned relative to the internal thread 5 until the axes 16, 17 are finally aligned and the clamp screw can be straightly and correctly screwed into the internal thread 5.

FIG. 4 illustrates a flank 21 in the widened lead-in region 18 and a flank 22 of the thread turn portions outside the lead-in region. FIG. 4 also illustrates a slightly deviating embodiment of the widened lead-in region 18. In this embodiment, the lead-in region 18 extends less far into the first thread turn portion 10 in the peripheral direction. Moreover, the widening in the axial direction is smaller than in the embodiment of FIG. 3. This entails little weakening of the axial thickness of the thread land 20 on the lead-in side 14 between the first thread turn portion 10 and the third thread turn portion 12. Another difference consists in the fact that the thread turn of the internal thread 5 is configured to have an L-shaped cross-section.

The invention claimed is:

1. A bone screw comprising:
   A. a screw head; and
   B. a receiving sleeve or tulip provided on the screw head, the receiving sleeve or tulip having a proximal-most end and a distal-most end and comprising:

i. two sleeve flanks, each sleeve flank provided with an internal thread; and
ii. a seat for a longitudinal support for surgical connection of adjacent bone screws, the seat formed between the two sleeve flanks, the internal thread of at least one of the two sleeve flanks comprising a thread entry, a thread turn and a thread lead-in side, and the thread turn comprising a widened lead-in region at the thread entry and a residual thread turn, the widened lead-in region on the thread lead-in side being widened relative to the residual thread turn to facilitate correct attachment of a clamp screw or set screw to the receiving sleeve or tulip, the widened lead-in region having a first flank, the first flank being inclined in a circumferential direction relative to a second flank in a further run of the residual thread turn outside the widened lead-in region, the internal thread of the at least one of the two sleeve flanks formed between the proximal-most end and the distal-most end of the receiving sleeve or tulip, and the thread turn and the widened lead-in region beginning below a proximal-most end of the receiving sleeve or tulip.

2. The bone screw according to claim 1, wherein the widened lead-in region is widened in an axial direction.

3. The bone screw according to claim 1, wherein the first flank rises into said internal thread of said at least one of the two sleeve flanks.

4. The bone screw according to claim 3, wherein an inclination of the first flank is flatter than an inclination of the second flank, wherein the inclination of the first flank corresponds to 0.5 times to 0.9 times the inclination of the second flank.

5. The bone screw according to claim 1, wherein a cross-sectional area in a radial direction of the thread turn at the thread entry corresponds to 1.7 times to 1.2 times a cross-sectional area of the thread turn outside the widened lead-in region.

6. The bone screw according to claim 1, wherein the widened lead-in region extends in a circumferential direction over a radial portion through an angle of between 20° and 135° relative to an axis of the internal threads.

7. The bone screw according to claim 1, wherein the internal thread of each of the two sleeve flanks is an undercut thread, or wherein the thread turn has a T-shaped or L-shaped cross-section.

8. The bone screw according to claim 1, wherein a thickness in an axial direction of a thread land located between the widened lead-in region and an adjacent thread turn is reduced as compared to a thickness of a thread land between adjacent thread turns by less than 50%.

9. The bone screw according to claim 1, wherein the receiving sleeve or tulip is formed integrally with the bone screw, or wherein the receiving sleeve or tulip is arranged to be positioned relative to the bone screw on the bone screw.

10. A method of manufacturing a bone screw according to claim 1, wherein the widened lead-in region is formed by milling.

11. The bone screw according to claim 1, wherein the thread entry forms a ramp configured to guide or lift a clamp screw or set screw initially obliquely attached or tilted during attachment, when the clamp screw or set screw is further screwed into the thread turn at the thread entry, and to align the clamp screw or set screw coaxially with respect to the internal thread of each sleeve flank of the receiving sleeve or tulip.

12. The bone screw according to claim 1, wherein the widened lead-in region is widened in a radial direction.

13. The bone screw according to claim 1, wherein said internal thread of the at least one of the two sleeve flanks comprises a first thread turn portion and a third thread turn portion, the first thread turn portion comprising the widened lead-in region at the thread entry, and the third thread turn portion having a constant cross section.

14. The bone screw according to claim 1, wherein the bone screw head and the receiving sleeve or tulip are formed as one-piece.

15. The bone screw according to claim 1, wherein the receiving sleeve or tulip engages the screw head.

16. The bone screw according to claim 1, wherein the internal thread further comprises a second thread turn and a third thread turn, the second thread turn and third thread turn having a constant cross-section.

17. A bone screw comprising:
A. a screw head; and
B. a receiving sleeve or tulip provided on the screw head, the receiving sleeve or tulip comprising:
i. two sleeve flanks, each sleeve flank provided with an internal thread; and
ii. a seat for a longitudinal support for surgical connection of adjacent bone screws, the seat formed between the two sleeve flanks, the internal thread of at least one of the two sleeve flanks comprising a thread entry, a thread turn and a thread lead-in side, and the thread turn comprising a widened lead-in region at the thread entry and a residual thread turn, the widened lead-in region on the thread lead-in side being widened relative to the residual thread turn to facilitate correct attachment of a clamp screw or set screw to the receiving sleeve or tulip, the widened lead-in region having a first flank, the first flank being inclined in a circumferential direction relative to a second flank in a further run of the residual thread turn outside the widened lead-in region, and the receiving sleeve or tulip being formed integrally with the screw head.

18. A bone screw comprising:
A. a screw head; and
B. a receiving sleeve or tulip provided on the screw head, the receiving sleeve or tulip comprising:
i. two sleeve flanks, each sleeve flank provided with an internal thread; and
ii. a seat for a longitudinal support for surgical connection of adjacent bone screws, the seat formed between the two sleeve flanks, the internal thread of at least one of the two sleeve flanks comprising a thread entry, a thread turn and a thread lead-in side, the thread turn comprising a widened lead-in region at the thread entry and a residual thread turn, the widened lead-in region on the thread lead-in side being widened relative to the residual thread turn to facilitate correct attachment of a clamp screw or set screw to the receiving sleeve or tulip, the widened lead-in region having a first flank, the first flank being inclined in a circumferential direction relative to a second flank in a further run of the residual thread turn outside the widened lead-in region, and the thread turn comprising an upper portion and a lower portion, the widened lead-in region extending upwardly from the lower portion of the thread turn.

* * * * *